(12) United States Patent
Craig et al.

(10) Patent No.: US 7,691,647 B2
(45) Date of Patent: Apr. 6, 2010

(54) COMPOSITIONS FOR USE AS A SIGNAL GENERATION COMPONENT AND METHODS OF USING SAME

(75) Inventors: Alan R. Craig, Wilmington, DE (US); Zhu Teng, Boothwyn, PA (US); Richard C. Wright, North East, MD (US); Chengrong Wang, Glen Mills, PA (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 0 days.

(21) Appl. No.: 11/499,519

(22) Filed: Aug. 4, 2006

(65) Prior Publication Data

US 2006/0270063 A1 Nov. 30, 2006

Related U.S. Application Data

(62) Division of application No. 11/040,887, filed on Jan. 21, 2005.

(51) Int. Cl.
*G01N 33/553* (2006.01)
*G01N 33/548* (2006.01)
*G01N 33/543* (2006.01)
*G01N 33/546* (2006.01)
*G01N 33/24* (2006.01)
*C07C 49/15* (2006.01)
*C07C 49/215* (2006.01)

(52) U.S. Cl. ............... 436/525; 436/529; 436/523; 436/533; 436/82; 435/968; 568/308; 568/326; 568/327; 568/328

(58) Field of Classification Search ............... 436/523, 436/533, 546, 82; 435/968, 7.1, 7.92

See application file for complete search history.

(56) References Cited

U.S. PATENT DOCUMENTS 4,220,450 A 9/1980 Maggio (Continued)

FOREIGN PATENT DOCUMENTS

EP 0 064484 A2 11/1982

(Continued)

OTHER PUBLICATIONS

Chen et al. Switching luminescent properties in osmium-based beta-diketonate complexes. ChemPhyChem 2005, vol. 6, pp. 2012-2017.*

(Continued)

*Primary Examiner*—Shafiqul Haq
(74) *Attorney, Agent, or Firm*—Theodore J. Leitereg; Robert N. Carpenter

(57) ABSTRACT

Compositions suitable for use as signal generation components of an immunoassay, and methods for their use. According to one aspect of the invention, the composition includes a carrier having a coating of an aminodextran and a metal chelate incorporated therein. The metal chelate is present in the amount of at least 0.065 µMole per gram of carrier, and the aminodextran coating density averaging at least about 45 µg per milligram of carrier. In another aspect of the invention, carrier is dyed with a complex having the formula:

$M(L1)_x(L2)_y$, wherein M is a metal selected from the group consisting of europium, terbium, dysprosium, samarium, osmium and ruthenium;

L1 is a ligand selected from the group consisting of DPP, TOPO, TPPO;

L2 comprises a ligand having the formula

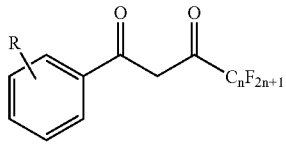

Formula 1 wherein R is one or more substituents, each substituent comprising an electron donating group; n=2-10; x=1-2; and y=2-4.

13 Claims, 4 Drawing Sheets

U.S. PATENT DOCUMENTS

| | | | |
|---|---|---|---|
| 4,283,382 | A | 8/1981 | Frank et al. |
| 4,565,790 | A | 1/1986 | Hemmila et al. |
| 4,587,223 | A | 5/1986 | Soini et al. |
| 4,637,988 | A | 1/1987 | Hinshaw et al. |
| 4,925,804 | A | 5/1990 | Hale et al. |
| 4,978,625 | A | 12/1990 | Wagner et al. |
| 5,316,909 | A | 5/1994 | Xu |
| 5,578,498 | A | 11/1996 | Singh et al. |
| 5,639,620 | A | 6/1997 | Siiman et al. |
| 5,707,877 | A | 1/1998 | Siiman et al. |
| 5,709,994 | A | 1/1998 | Pease et al. |
| 5,811,311 | A | 9/1998 | Singh et al. |
| 6,080,839 | A | 6/2000 | Takalo et al. |
| 6,165,729 | A | 12/2000 | Leland et al. |
| 6,339,172 | B1 | 1/2002 | Matsui et al. |
| 6,399,397 | B1 | 6/2002 | Zarling et al. |
| 2001/0055763 | A1 | 12/2001 | Singh |
| 2001/0055776 | A1 | 12/2001 | Greenwalt |
| 2002/0055763 | A1 | 5/2002 | Zarinetchi et al. |
| 2002/0106674 | A1 | 8/2002 | Matsui et al. |
| 2002/0150929 | A1 | 10/2002 | Matsumoto et al. |
| 2003/0133972 | A1 | 7/2003 | Danthi et al. |
| 2004/0082768 | A1 | 4/2004 | Murthy et al. |

FOREIGN PATENT DOCUMENTS

| | | |
|---|---|---|
| EP | 0 515194 A2 | 11/1992 |
| WO | WO 01/67105 | 9/2001 |
| WO | WO 03/000933 A1 | 1/2003 |

OTHER PUBLICATIONS

Yuan et al New Tetradentate B-Diketonate-Europium Chelate that can be Convalently Bound to Proteins for Time-Resolved Fluoroimmunoassay Anal Chem 1998, vol. 70, pp. 596-601.

Phelan et al. Organic light emitting diodes incorporating nanometer thick films of europium cored complexes. Proceedings of SPIE, 2002, vol. 4809, pp. 179-189.

U.S. Appl No. 10/220,623, Kirakossian.

Matsumoto et al., "Simultaneous Determination of a-Fetoprotein . . . ", Analytical Biochemistry, vol. 276, p. 81-87 (1999).

Sueda et al., "Homogeneous DNA Hybridization Assay Luminescence Energy Transfer", Bioconjugate Chem, vol. 11, p. 827-831 (2000).

* cited by examiner

COMPOSITIONS FOR USE AS A SIGNAL GENERATION COMPONENT AND METHODS OF USING SAME

This application is a Division of U.S. Ser. No. 11/040,887 filed Jan. 21, 2005.

FIELD OF THE INVENTION

The present invention relates generally to compositions useful as signal generation components in immunoassays. In particular, the invention relates to compositions that simultaneously provide a strong signal as well as an enhanced specificity for the analytes of interest.

BACKGROUND OF THE INVENTION

Immunoassay reagents have functionality that can be broken down into two broad components: signal generation (also known as amplification) functionality, and ligand binding functionality. The signal generation functionality is required for detection of ligand binding to analyte, and the ligand binding functionality is the specificity of the reagent for the analyte. The ligand binding activity is accomplished by covalently attaching ligands to the particle surface. Antibodies and small haptens of biological significance, such as thyroxin, are examples of common ligands.

Fluorescent and chemiluminescent compositions have been widely used in signal generation components of immunoassays. A typical signal generation component includes a carrier, such as a latex particle, dyed with a fluorescent or chemiluminescent composition. In particular, metal chelates have been widely used as fluorescent and chemiluminescent dyes because of their generally large stokes' shift, sharp emission peak and long emission wavelength. Typically, the metal chelates are a complex formed of a metal, such as europium, samarium, or terbium, and ligands such as thiophenetrifluorobutanedione (TTA), napthyltriflurobutanedione (NTA), and 4,7-diphenyl-1,10-phenathroline (DPP) trioctyl phosphine oxide (TOPO), triphenyl phosphine oxide (TPPO). Some commonly used metal chelates include $Eu(TTA)_3DPP$ and $Eu(NTA)_3DPP$.

Dyed carriers that are used to make assay reagents must have both the capability to provide signal generation, and the chemical functionality for covalent attachment of ligands. The process used to attach the ligands can be critical to the quality of the specificity of the ligand binding functionality. The specificity of the ligands can be compromised in several ways by inappropriate choices of attachment chemistry. For example, if passive adsorption of the ligands occurs simultaneously with covalent attachment, the passively adsorbed ligands may come off of the carrier during the assay. The resulting free ligand will interfere with the assay and reduce its sensitivity. Another problem that can occur is the non-specific binding of the reagent to the other carrier, which leads to elevation of the immunoassay signal in the absence of analyte.

Ligands are often attached to polystyrene particles through carboxy groups that are attached directly to the surface of the particles. This approach can have both of the problems described above. The passive adsorption and nonspecific binding problems can be avoided by introducing one or more layers of immobilized hydrogel polymers, such as an aminodextran, between the polystyrene particles and the ligands. It is important for elimination of adsorption and nonspecific binding to have a continuous layer of these hydrogel polymers.

However, the coating of particles that are dyed with conventional dyes such as $Eu(TTA)_3DPP$ or $Eu(NTA)_3DPP$ typically result in coating densities of aminodextran that are significantly less than optimal for preventing non-specific binding. The coupling density of the aminodextran is typically reduced by 40-50% from its maximum when these dyes are added at the optimum level for the chemiluminescent response of the reagent. Lower levels of dye give compositions that interfere less with the aminodextran coating process, but reducing the dye content also reduces the chemiluminescence necessary for a strong signal.

Accordingly, there remains a need in the art to provide a more optimal balance between the amplitude of the response signal and the specificity of the signal generation components in an specific binding assay.

SUMMARY OF THE INVENTION

The compositions of the present invention provide signal generation components having an optimal balance between the reduction of non-specific binding while allowing an improved response signal.

According to one aspect of the invention, a composition suitable for use as a signal generation component in an immunoassay is provided. The composition includes a carrier having a coating of an aminodextran and dyed with a metal chelate. The metal chelate is present in the amount of at least 0.065 μMole per gram of carrier, and the average aminodextran coating density is at least about 45 μg per milligram of carrier.

A composition according to another aspect of the invention includes a carrier coated with an aminodextran and with a complex incorporated therein having the formula:

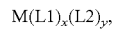

wherein M is a metal selected from the group consisting of europium, terbium, dysprosium, samarium, osmium and ruthenium;

L1 is a ligand selected from the group consisting of DPP, TOPO, and TPPO;

L2 comprises a ligand having the formula

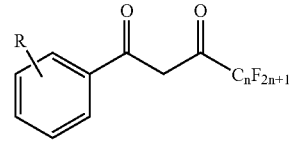

Formula 1 wherein R is one or more substituents, each substituent comprising an electron donating group; and n=2-10, x=1-2 and y=2-4.

According to another aspect of the invention, a method of detecting the presence or amount of an analyte in a test sample suspected of containing the analyte is provided. The method comprises performing an immunoassay using the compositions of the present invention as a signal generating component.

The foregoing paragraphs have been provided by way of general introduction, and are not intended to limit the scope of the following claims. The presently preferred embodiments, together with other aspects of the invention, will be best understood by reference to the following detailed description taken in conjunction with the accompanying drawings.

DETAILED DESCRIPTION OF THE PREFERRED EMBODIMENTS

Figure 1:
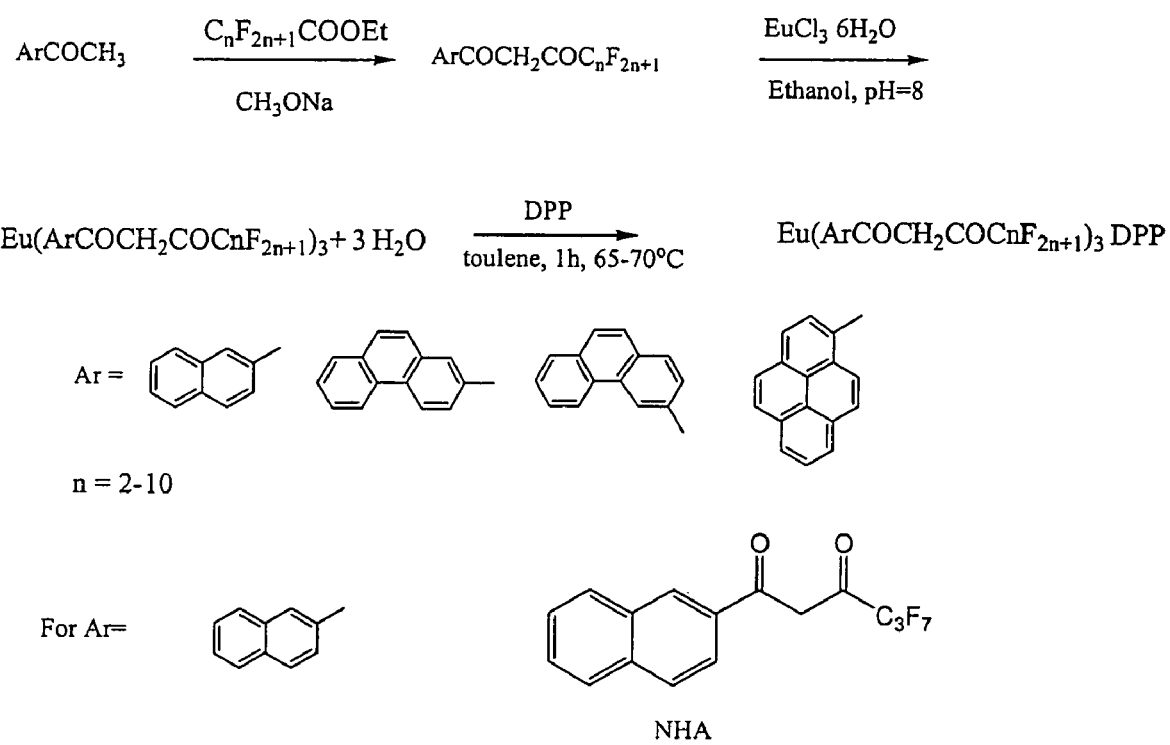
FIG. 1 is a schematic illustrating the synthesis of one embodiment of a metal chelate according to the present invention.

The compositions of the present invention are useful as signal generation components in immunoassays. The compositions generally include a carrier coated with an aminodextran and have a metal chelate incorporated therein. The compositions provide strong response signals which allows for quantitative determinations of analytes of interest, while reducing errors caused by non-specific binding.

Carriers suitable for the present invention include solid phase materials, typically a support or surface, that can have any one of a number of shapes, such as strip, sheet, rod, plate, well, tube, particle or bead. The material is usually of an organic or inorganic, swellable or non-swellable, porous or non-porous, magnetic or non-magnetic, water-insoluble material. The surface can be hydrophilic or capable of being rendered hydrophilic. The solid support includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, polyvinylchloride, polyacrylamide, crosslinked dextran, agarose, polyacrylate, polyethylene, polypropylene, poly(4-methylbutene), polystyrene, polymethacrylate, polyethyleneterephthalate, nylon, polyvinylbutyrate, etc.; either used by themselves or in conjunction with other materials; glass available as Bioglass, ceramics, magnetic materials, metals, and the like. Natural or synthetic assemblies such as liposomes, phospholipid vesicles, and cells can also be employed.

In one embodiment of the present invention, the carrier is a particle. "Particle", as used herein, encompasses spheres, spheroids, beads and other shapes as well. Suitable particles are typically at least 20 nm and not more than about 20 µm, usually at least about 40 nm and less than 10 µm, preferably 0.1 to 10 µm, more preferably, 0.1 to 5 µm, and even more preferably 0.15 to 3 µm. The particle may be organic or inorganic, swellable or non-swellable, porous or non-porous, having any density, but preferably of a density approximating water, generally from about 0.7 to about 1.5 g/ml, preferably suspendable in water, and composed of material that can be transparent, partially transparent, or opaque. The particles may be core-and-shell particles, such as particles with a magnetic core and a hard shell coating of polymerized monomer (s). The particles are preferably negative charged. The particles are preferably solid, e.g., polymer particles, metal sols (particles comprised of a heavy metal such as, e.g., gold or silver), glass particles, silicon particles; magnetic particles, dye crystallites.

One especially preferred particle is a latex particle. "Latex", as used herein, means a particulate water-suspendable water-insoluble polymeric material. The latex is frequently a substituted polyethylene such as: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The carriers according to the present invention are coated with one or more layers of an aminodextran. An aminodextran is a derivatized glucose polymer with amino groups having a molecular weight of about 10,000 to about 2,000,000, preferably about 500,000. Methods of preparing aminodextrans and coating carriers are known in the art. Suitable methods are described in U.S. Pat. No. 5,707,877, columns 18-20, and U.S. Pat. No. 5,639,620, columns 21 and 22.

In one preferred method, aminodextran is coated on the carrier by covalent attachment of the amino group of aminodextran to the surface carboxyl groups or other amine-reactive functional group of the carrier. Such a method is described in provided in commonly-assigned and copending U.S. Ser. No. 10/220,623, filed Mar. 6, 2000 entitled "Carriers Coated with Polysaccharides, Their Preparation and Use," the entire disclosure of which is incorporated herein by reference.

The aminodextran coating improves the specificity of the carrier in specific binding assays and therefore improves the sensitivity of immunoassays. It has been discovered that the metal chelate of the present invention unexpectedly allows for coating of carriers with aminodextran in the amount of at least about 45 µg per milligram of carrier in the presence of a dye concentration as high as at least 0.065 µMole per gram. According to one preferred embodiment of the present invention, the aminodextran coating is present in at least about 49 µg per milligram of carrier.

In one preferred embodiment of the invention, the carrier may be coated with a second layer comprising a polysaccharide, as described in U.S. Ser. No. 10/220,623. The polysaccharide may be covalently coupled to the aminodextran layer by amine-reactive functional groups. In one preferred embodiment, the second layer comprises dextran aldehyde.

A metal chelate is incorporated into the carrier through a known process, such as dyeing. The metal chelate allows for a fluorescent or chemiluminescent signal to be detected. The metal chelate is chosen such that relatively higher concentrations of the metal chelate do not interfere with the binding of the aminodextran coating to the carrier. According to one embodiment of the present invention, the metal chelate is present in the amount of at least 0.065 µMole per gram of carrier, while the aminodextran average coating density is at least about 45 µg per milligram of carrier. In another embodiment of the invention the metal chelate is present in the amount of at least 0.065 µMole per gram of carrier and less than about 0.150 µMole per gram of carrier, more preferably about 0.079 µMole per gram of carrier to about 0.150 µMole per gram of carrier, and more preferably about 0.087 µMole per gram of carrier. In another embodiment of the invention, the metal chelate is present in the amount of about 0.1110 µMole per gram of carrier to about 135 µMole per gram or carrier. These concentrations of metal chelate and aminodextran have been found to provide a proper balance of response signal and component specificity for the analyte of interest.

According to one embodiment of the present invention, the metal chelate has the general formula

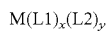

wherein M is a metal selected from the group consisting of europium, terbium, dysprosium, samarium, osmium and ruthenium;

L1 is a ligand selected from the group consisting of DPP, TOPO, and TPPO;

L2 comprises a ligand having the formula

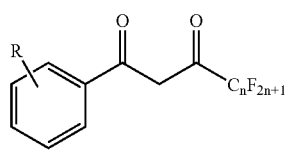

Formula 1 wherein R is one or more substituents, each substituent comprising an electron donating group;

n=2-10;
x=1-2; and
y=2-4.

Suitable electron donating groups are those that make available extra negative charge to the perfluoralkyl groups. In one embodiment, the electron donating group R is selected from the group consisting of $C_1$ to $C_6$ alkyls, dialkylamines, ethers, thioethers, and aryl groups.

Without desiring to be bound by theory, it is believed that the metal chelates of the present invention are effective in allowing optimized amounts of aminodextran to coat the carrier because the metal chelates provide an unexpectedly stable complex relative to prior metal chelate dyes. The stability of the complex reduces the amount of the free metal, which is believed to inhibit the attachment of the aminodextran to the carrier. It is also believed that electron donating groups R further add to the stability of the complex by making available additional negative charge to the perfluoroalkyl groups of the ligands, thereby improving the ability of the perfluoralkyl group to bind to the metal in the complex.

According to one particular embodiment of the invention, M is europium and the carrier is a latex particle. According to preferred embodiments of the invention, n=3 or 7, and x=1 and y=3.

According to specific embodiments of the invention, L2 is selected from among the following formulas:

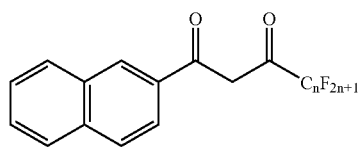

Formula 2

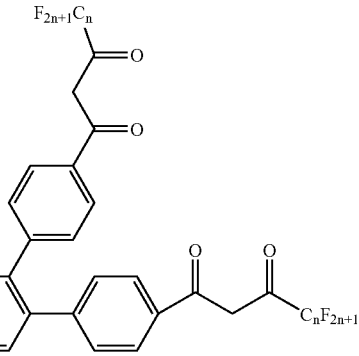

Formula 3

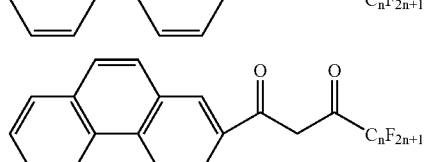

Formula 4

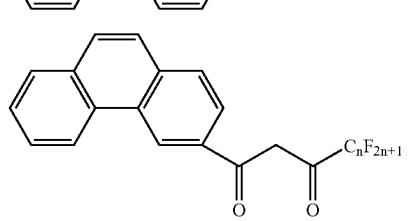

Formula 5

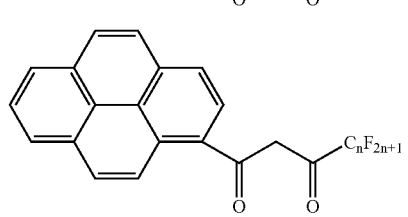

Formula 6

In a preferred embodiment of the above described ligands, n=3 or n=7. In a preferred embodiment of the invention, the ligands L2 are 2-(1',1',1',2',2',3',3'-heptafluoro-4',6'-hexanedion-6'-yl)-naphthylene (NHA) and 4,4'-bis(2",3",3"-heptafluroro-4",6"-hexanedion-6"-yl)-o-terphenyl (BHHT).

Figure 2:
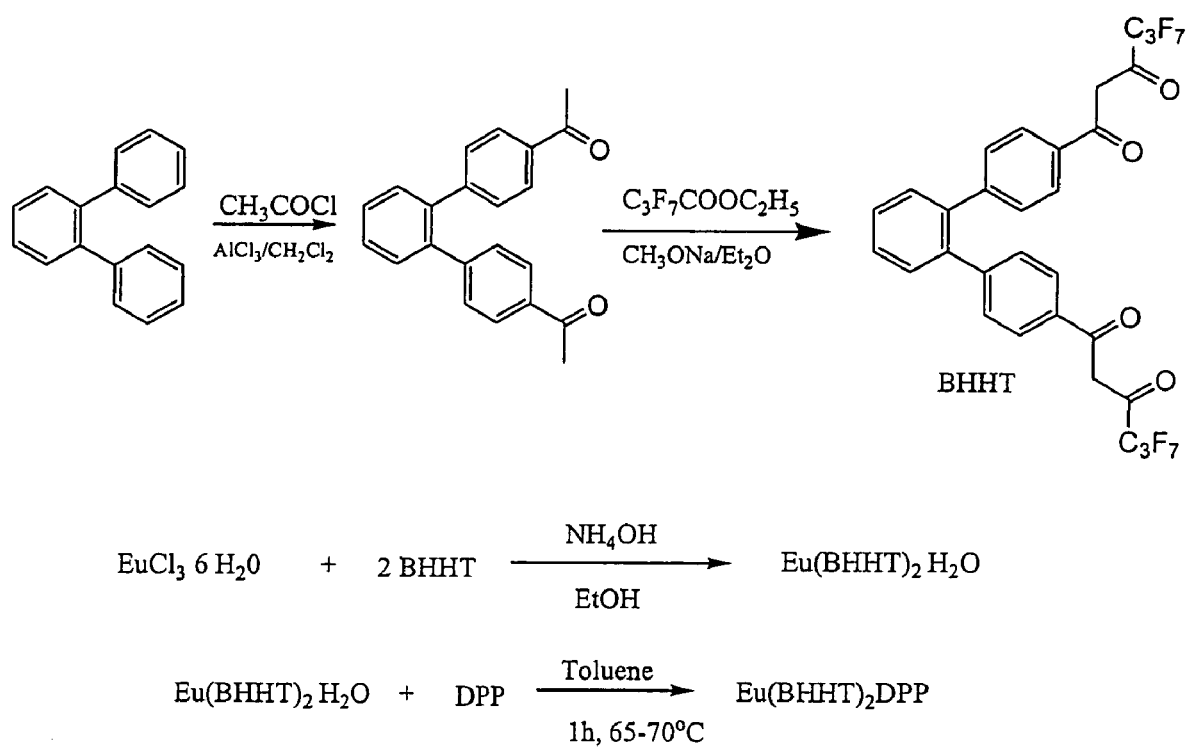
FIG. 2 is a schematic illustrating the synthesis of another embodiment of a metal chelate according to the present invention.

In a particularly preferred embodiment of the present, the metal chelate comprises $Eu(NHA)_3DPP$ and $Eu(BHHT)_2DPP$. Generally, the metal chelates can be prepared by combining the metal chloride with the desired ratio of metal ligand molecules in an organic solvent and sufficient base to take up the released hydrochloric acid. Suitable syntheses are illustrated in FIGS. 1-2, respectively.

The metal chelate dyes of the present invention have been found to allow for a higher density of aminodextran coating at relatively higher concentrations of the metal chelate dyes when compared to conventional dyes, as demonstrated in the Comparative Examples below. At constant optimized dye concentrations, the metal chelates of the present invention generally will allow an aminodextran coating at about 45 to about 55 μg per mg beads compared to about 23 to about 35 μg per mg of bead for the conventional dyes. Accordingly, the dyes of the present invention can be present in amounts sufficient to give strong response signals as part of a signal generation component in a specific binding assay, while allowing the carrier to be coated with an aminodextran in an amount sufficient to reduce the amount of non-specific binding.

The compositions of the present invention are suitable for use as a signal generation component in specific binding assays. The compositions are suitable for any immunoassay in which a signal is measured in response to ligand binding to an analyte. Those skilled in the art will readily appreciate the compositions have wide utility in a number of assay formats.

In one embodiment of a specific binding assay according to the present invention, the signal generating component is used to perform Luminescent Oxygen Channeling Immunoassay (LOCI™) as described in EP-A2-0 515 194. In this method for the qualitative or quantitative determination of an analyte, at least one specific binding partner is bound to a carrier according to the present invention. A medium suspected of containing an analyte is treated under conditions such the analyte affects the amount of a sensitizer capable in its excited state of generating singlet oxygen and a chemiluminescent compound that can come into close proximity such that singlet oxygen generated by said photosensitizer can activate said chemiluminescent compound, which subsequently produces light, and measuring the light, the amount thereof being related to the amount of analyte in said medium.

In another embodiment, the LOCI™ method, includes the steps of: (A) combining either simultaneously or wholly or partially sequentially (i) a medium suspected of containing the analyte; (ii) a first specific binding partner associated with a sensitizer capable in its excited state of generating singlet oxygen; and (iii) a second specific binding partner associated with a composition comprising a chemiluminescent compound, which is a substance that undergoes a chemical reaction with singlet oxygen to form a metastable intermediate species that can decompose with the simultaneous or subsequent emission of light; (B) allowing the formation of complexes comprising the first and the second specific binding partner, the complex formation brings the sensitizer into close proximity to the chemiluminescent compound, (C) activating the sensitizer to generate singlet oxygen; and measuring the amount of light emitted by the chemiluminescent compound, the light is directly or inversely proportional to the amount of analyte in the medium. The composition comprising the chemiluminescent compound can also comprise one or more fluorescent molecules which are excited by the activated chemiluminescent compound. The light emitted by said fluorescent molecules can be measured to determine the amount of analyte in the medium.

In one embodiment of the invention using the LOCI method, the carrier may be dyed both with a metal chelate and an oxygen acceptor. The oxygen acceptor is a component that reacts with singlet oxygen to form a highly unstable product that rapidly decomposes into an excited state. The excess energy of the excited state is transferred to the dye by a Forster energy transfer that takes place in a few nanoseconds. The metal chelate dye then emits a photon of light that can be detected with a photon counter. Suitable oxygen acceptors are disclosed in U.S. Pat. Nos. 5,578,498 and 5,811,311. One particularly preferred oxygen acceptor is C-28 thioxene, which has the following formula:

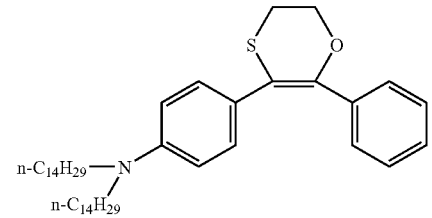

Formula 7

EXAMPLE

Preparation of Single Generation Component

A mixture of 100 mL 10% solution of carboxylated latex beads (from Seradyn), 138 ml 1-methoxy-2-propanol, 280 mL D.I. water and 10 mL of 0.1 M NaOH is placed in a three-necked flask equipped with a mechanical stirrer and a thermometer. The mixture is brought to 80° C. with stirring. A separate solution is then prepared with a 2 g of C-28 thioxene and 2.7 g Eu(NHA)$_3$DPP in 220 mL of 1-methoxy-2-propanol, and the solution is heated to 80° C. with stirring until dissolved. The dye solution is then poured into the bead solution and stirred for 30 min. at 80° C. and then allowed to cool slowly to 40° C. The beads are then washed by diafiltration with 10% v/v ethanol in water adjusted to pH 10 with NaOH. The beads are then concentrated to about 20 mg/ml during the wash, and then stored at 4° C. protected from light.

The aminodextran coating is then applied as follows. 1 mL of the dyed beads (~20 mg/ml) is mixed with 20 mg/ml of hydroxypropylaminodextran (MW 500K) in 0.05M MES/pH 6.0 in the presence of 3.8 mg/ml EDAC. After incubating this mixture for 16 hours at room temperature, (in the dark) the beads were washed once with 2 ml of 0.05M MES/pH 6.0, then with 6 ml of 0.05M MES, 1.0M NaCl/pH 6.0. Finally the beads were resuspended in 1 ml of 0.05M MES/pH 6.0 to yield the coated beads. Washing was performed by centrifugation method (using Sorval RC-5B Plus centifruge or Ependorf centrifuge-5415 C) and pellets were resuspended by sonication (using Branson Sonifer-450).

The dextran aldehyde layer may then be added as follows. 1 ml of the 20 mg/ml dextran aldehyde in 0.05M MES is mixed with 1 ml of the aminodextran coated chemiluminescent beads in the presence of 2 mg/ml NaBH$_3$CN. After incubating for 37° C. for 20 hours (in the dark), the beads were washed once with 4 ml and then with another 5 ml of MES buffer. The beads were resuspended in 0.5 ml of 0.05MES, 0.4% Tween-20/pH 6.0 to yield about 40 mg/ml of coated beads.

Comparative Example 1

A first set of latex particles were dyed with Eu(NTA)$_3$DPP and thioxene and coated with an aminodextran according to the methods described herein. Likewise, a second set of latex particles were dyed with Eu(NHA)$_3$DPP and thioxene and coated with an aminodextran.

For each of the compositions, the aminodextran coating densities and the chemiluminescence were simultaneously measured at several concentrations of the metal chelate. The aminodextran coating density was measured by a colorimetric test after being treated with anthrone and 80% sulfuric acid. The chemiluminescence was measured as LOCI counts by an by an Envision-Alpha reader sold by Perkin-Elmer. The data points for Eu(NTA)₃DPP are tabulated in Table 1 and shown graphically with curve fitting in FIG. 3. The data points for Eu(NHA)₃DPP are tabulated in Table 2 and, for concentrations up to 0.094, are shown graphically with curve fitting in FIG. 4.

TABLE 1

LOCI counts and aminodextran concentration as a function of europium concentration in Eu (NTA)₃DPP

| Eu (mMole/g beads) | Aminodextran coating (μg/mg beads) | LOCI signal, MM counts |
|---|---|---|
| 0.169 | 30 | 9.7 |
| 0.085 | 36 | 9.2 |
| 0.042 | 45 | 6.7 |
| 0.021 | 55 | 2.8 |
| 0.000 | 62 | 0.0 |

TABLE 2

LOCI counts and aminodextran concentration as a function of europium concentration in Eu (NHA)₃DPP

| Eu (mMole/g beads) | LOCI signal, MM counts | Andex coating (μg/mg beads) |
|---|---|---|
| 0.020 | 3.8 | 60 |
| 0.028 | 5.3 | 57 |
| 0.035 | 6.6 | 55 |
| 0.043 | 7.7 | 53 |
| 0.050 | 8.6 | 51 |
| 0.057 | 9.4 | 50 |
| 0.065 | 10.0 | 49 |
| 0.072 | 10.5 | 49 |
| 0.079 | 10.8 | 49 |
| 0.087 | 10.9 | 50 |
| 0.094 | 10.8 | 50 |
| 0.0135* | 10.8* | 50* |

Figure 4:
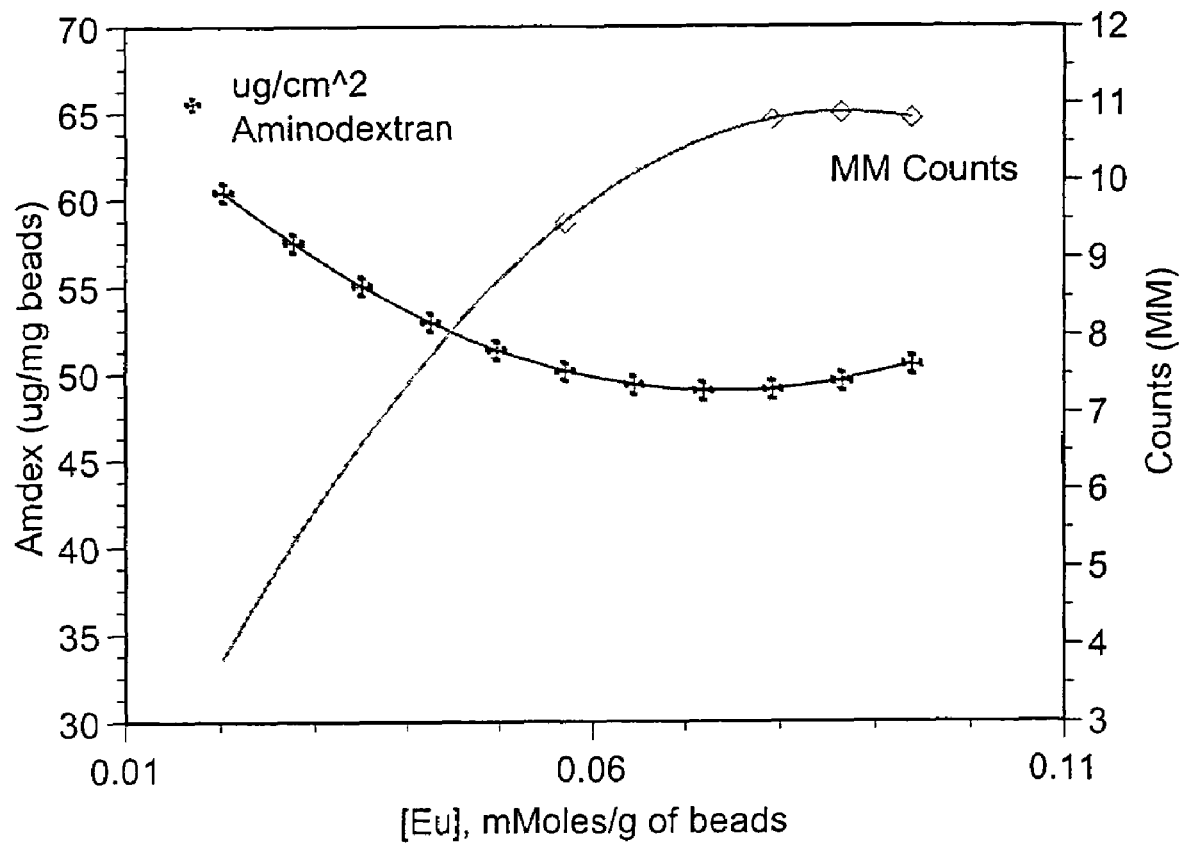
FIG. 4 is a graphical representation of aminodextran concentration and response signal as functions of metal concentration for compositions according to the present invention.

*results not shown in FIG. 4

Figure 3:
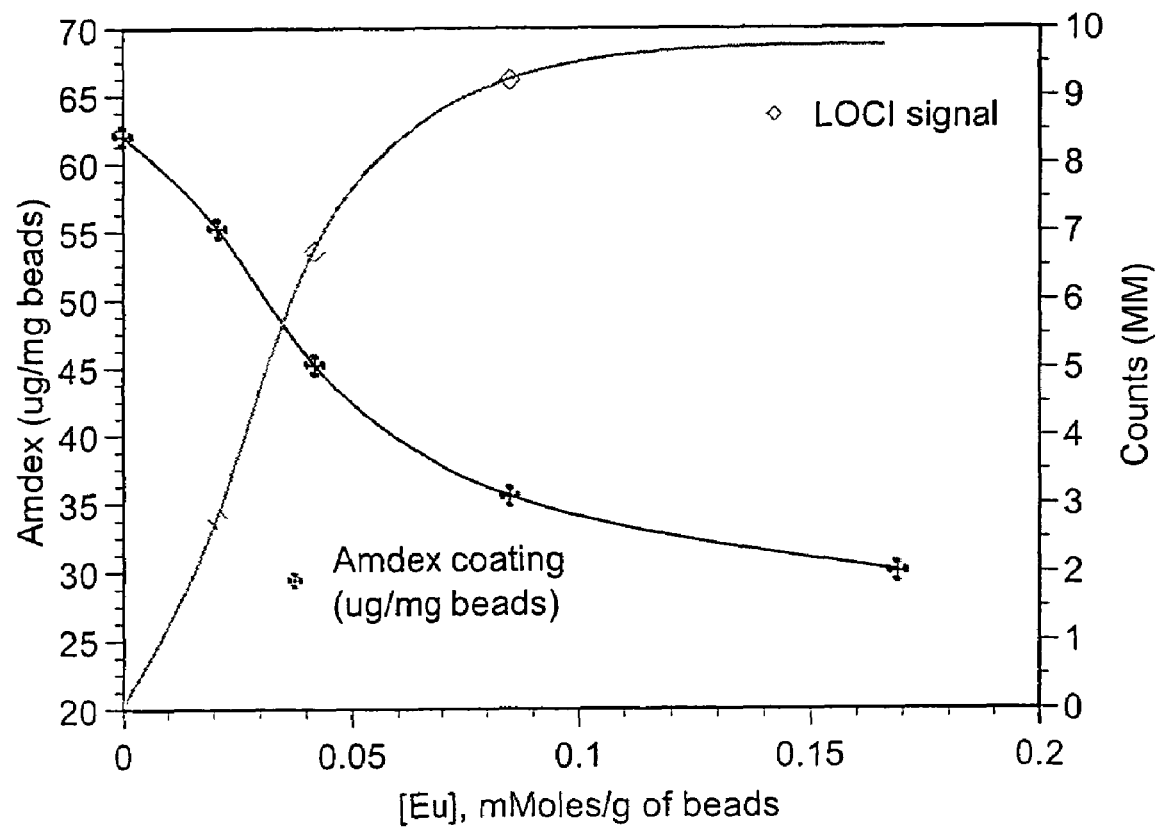
FIG. 3 is a graphical representation of aminodextran concentration and response signal as functions of metal concentration for a prior art composition.

As can be seen from FIG. 3, in the prior art composition, the aminodextran loading and the LOCI signal could not be simultaneously poised on a plateau for response with respect to composition. The response signal does not begin to plateau until about 0.085 mmoles Eu/gram of beads. At higher concentrations, the aminodextran coating concentration is only at 36 ug/mg of beads, and continues to decline with increasing europium concentrations.

In contrast, as shown in FIG. 4, the compound according to the present invention begins to plateau both in terms of aminodextran concentration and LOCI signal with as little as 0.065 μMole Eu/gram of beads. At this concentration, the average aminodextran coating concentration is 49 μg/mg beads. Furthermore, the concentration of aminodextran generally holds steady as the concentration of europium is increased.

Comparative Example 2

Latex beads from Seradyn were dyed with 0.171 mmol of Europium dye and 0.303 mmol of C-28 thioxene per gram of bead for each of two conventional dyes, Eu(TTA)₃DPP and Eu(NTA)₃DPP and two dyes according to the present invention, Eu(BHHT)₂DPP and Eu(NHA)₃DPP. The beads were then coated with aminodextran as described herein. The densities of the aminodextran was then determined, as well as the amplitude of its response signal. The data are tabulated on Table 3.

All of the signal generation components provided adequate signal, as measured by LOCI counts. However, the dyes of the present invention yield a significantly higher range of coating densities of aminodextran.

TABLE 3

Europium Complex Dyed Particles Aminodextran Coating Density

| Dye Type | Aminodextran coating densities (ug/mg bead) | LOCI counts (MM) |
|---|---|---|
| Eu(TTA)₃DPP | 21-44 | 8.4-13.3 |
| Eu(NTA)₃DPP | 30-47 | 6.8-9.6 |
| Eu(BHHT)₂DPP | 63-69 | 9.9-10.3 |
| Eu(NHA)₃DPP | 48-60 | 5.9-9.1 |

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

The invention claimed is:

1. A composition suitable for use as a signal generation component in an immunoassay comprising:
   a carrier coated with an aminodextran, wherein the density of the aminodextran averages at least about 45 μg per milligram of carrier, and having incorporated therein, at a concentration of at least 0.065 μMole per gram of the carrier, a complex having the formula:

$M(L1)_x(L2)_y$, wherein M is a metal selected from the group consisting of europium, terbium, dysprosium, samarium, osmium and ruthenium;
   L1 is a ligand selected from the group consisting of DPP, TOPO, TPPO;
   L2 comprises a ligand having the formula Formula 1

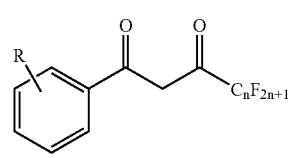

wherein R is one or more substituents, each substituent comprising an electron donating group;
   n=3 or 7;
   x=1-2; and
   y=2-4.

2. The composition of claim 1, wherein each R is independently selected from the group consisting of C1 to $C_6$ alkyls, dialkylamines, ethers, thioethers, and aryls.

3. The composition of claim 2, wherein M comprises europium.

4. The composition of claim 3, wherein the carrier comprises a latex particle.

5. The composition of claim 1, wherein n=3.

6. The composition of claim 2, wherein x=1 and y=3.

7. The composition of claim 1, wherein n=7.

8. The composition of claim 1, wherein L2 comprises

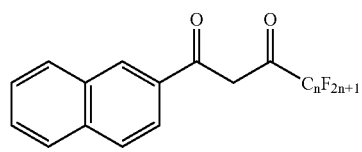

Formula 2

9. The composition of claim 1, wherein L2 comprises

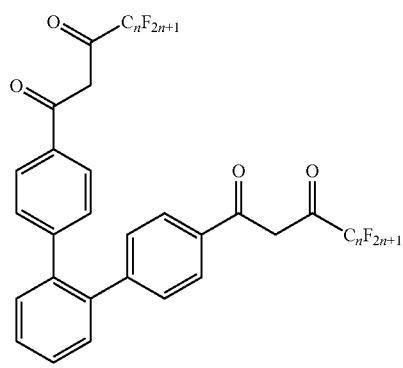

Formula 3

10. The composition of claim 1, wherein L2 comprises

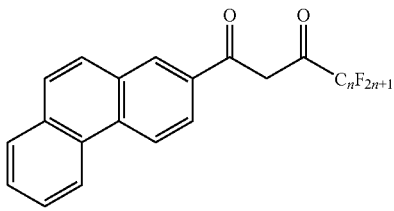

Formula 3

11. The composition of claim 1, wherein L2 comprises

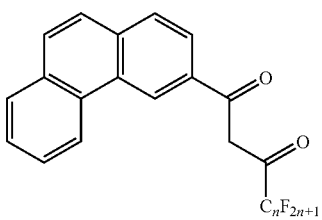

Formula 5

12. The composition of claim 1, wherein L2 comprises

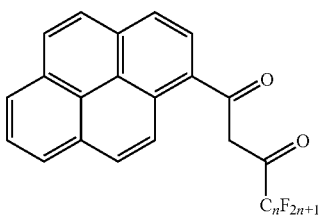

Formula 6

13. The composition of claim 1, wherein coating further comprises a second layer comprising a dextran aldehyde.

* * * * *

UNITED STATES PATENT AND TRADEMARK OFFICE
CERTIFICATE OF CORRECTION

Page 1 of 1

PATENT NO.      : 7,691,647 B2
APPLICATION NO. : 11/499519
DATED           : April 6, 2010
INVENTOR(S)     : Alan R. Craig et al.

It is certified that error appears in the above-identified patent and that said Letters Patent is hereby corrected as shown below:

Title Page, Item (57) Abstract, line 6, "μMole" should read --mMole--.
Column 2, line 28, column 4, lines 36, 54, 58-61 and 64, and column 9, line 51, each occurrence, "μMole" should read --mMole--.
Column 10, line 43 (in claim 1), "μMole" should read --mMole--.

Signed and Sealed this
Third Day of May, 2011

David J. Kappos
*Director of the United States Patent and Trademark Office*